(12) United States Patent
Wang

(10) Patent No.: US 9,200,266 B2
(45) Date of Patent: *Dec. 1, 2015

(54) METHODS AND COMPOSITIONS FOR TARGETED SINGLE-STRANDED CLEAVAGE AND TARGETED INTEGRATION

(71) Applicant: Sangamo BioSciences, Inc., Richmond, CA (US)

(72) Inventor: Jianbin Wang, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/199,753

(22) Filed: Mar. 6, 2014

(65) Prior Publication Data

US 2014/0212928 A1    Jul. 31, 2014

Related U.S. Application Data

(63) Continuation of application No. 12/583,329, filed on Aug. 18, 2009, now Pat. No. 8,703,489.

(60) Provisional application No. 61/189,800, filed on Aug. 22, 2008.

(51) Int. Cl.

| C12N 15/01 | (2006.01) |
|---|---|
| C12N 15/00 | (2006.01) |
| C12N 15/87 | (2006.01) |
| C12P 19/34 | (2006.01) |
| A61K 38/43 | (2006.01) |
| C07H 21/04 | (2006.01) |
| C07K 1/00 | (2006.01) |
| C12N 9/22 | (2006.01) |
| C12N 15/90 | (2006.01) |

(52) U.S. Cl.
CPC ............... *C12N 9/22* (2013.01); *C12N 15/907* (2013.01); *C07K 2319/70* (2013.01); *C07K 2319/81* (2013.01)

(58) Field of Classification Search
CPC ........... C07K 2319/70; C07K 2319/81; C12N 15/907; C12N 9/22
USPC ................ 435/440, 455, 463, 91.1; 424/94.1; 536/23.4; 530/350
See application file for complete search history.

(56) References Cited

U.S. PATENT DOCUMENTS

| 5,420,032 | A | 5/1995 | Marshall et al. |
|---|---|---|---|
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas et al. |
| 6,200,759 | B1 | 3/2001 | Dove et al. |
| 6,242,568 | B1 | 6/2001 | Barbas et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox et al. |
| 6,599,692 | B1 | 7/2003 | Case |
| 6,607,882 | B1 | 8/2003 | Cox, III et al. |
| 6,689,558 | B2 | 2/2004 | Case |
| 6,824,978 | B1 | 11/2004 | Cox, III et al. |
| 6,828,098 | B2 | 12/2004 | Langmore et al. |
| 6,833,252 | B1 | 12/2004 | Dujon et al. |
| 6,867,028 | B2 | 3/2005 | Janulaitis et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,081,358 | B2 * | 7/2006 | Heiter et al. ................. 435/199 |
| 7,153,949 | B2 | 12/2006 | Kim et al. |
| 7,163,824 | B2 | 1/2007 | Cox, III et al. |
| 7,244,560 | B2 | 7/2007 | Chestnut |
| 8,703,489 | B2 * | 4/2014 | Wang ............................ 435/463 |
| 2003/0232410 | A1 | 12/2003 | Liljedahl et al. |
| 2005/0026157 | A1 | 2/2005 | Baltimore |
| 2005/0064474 | A1 | 3/2005 | Urnov et al. |
| 2005/0208489 | A1 | 9/2005 | Carroll |
| 2006/0063231 | A1 | 3/2006 | Li et al. |
| 2006/0188987 | A1 | 8/2006 | Guschan et al. |
| 2007/0117128 | A1 | 5/2007 | Smith et al. |
| 2007/0134796 | A1 | 6/2007 | Holmes et al. |

(Continued)

FOREIGN PATENT DOCUMENTS

| GB | 2338237 A | 12/1999 |
|---|---|---|
| WO | WO 95/19431 A1 | 7/1995 |

(Continued)

OTHER PUBLICATIONS

Santiago et al., Targeted gene knockout in mammalian cells by using engineered zinc-finger nucleases. PNAS., 2008, vol. 105 (15): 5809-5814.*
Argast, et al., "I-PPOI and I-CREI Homing Siie Sequence Degeneracy Determined by Random Mutagenesis and Sequential In Vitro Enrichment," *J Mol Biol* 280:345-353 (1998).
Ashworth, et al., "Computational Redesign of Endonuclease DNA Binding and Cleavage Specificity," *Nature* 44:656-659 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucl Acids Res* 25:3379-3388 (1997).
Bitinate, et al., "FOKI Dimerization Is Required for DNA Cleavage," *PNAS USA* 95:10570-10575 (1998).
Caldecott, "Single-Strand Break Repair and Genetic Disease," *Nat Rev Genet* 9:619-631 (2008).
Chevalier, et al., "Design, Activity, and Structure of a Highly Specific Artificial Endonuclease," *Molec Cell* 10:895-905 (2002).
Choo, et al., "Advances in Zinc Finger Engineering," *Curr. Opin. Struct. Biol.* 10:411-416 (2000).

(Continued)

*Primary Examiner* — Ganapathirama Raghu
(74) *Attorney, Agent, or Firm* — Pasternak Patent Law; Susan Abrahamson

(57) ABSTRACT

Disclosed herein are methods and compositions for generating a single-stranded break in a target sequence, which facilitates targeted integration of one or more exogenous sequences.

12 Claims, 9 Drawing Sheets

(56) References Cited

U.S. PATENT DOCUMENTS

| | | |
|---|---|---|
| 2007/0218528 A1 | 9/2007 | Miller |
| 2008/0015164 A1 | 1/2008 | Collingwood |
| 2008/0131962 A1 | 6/2008 | Miller |
| 2009/0111119 A1 | 4/2009 | Doyon et al. |
| 2009/0263900 A1 | 10/2009 | DeKelver et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2005/014791 A2 | 2/2005 |
| WO | WO 2007/014275 A2 | 1/2007 |
| WO | 2007-136685 A2 | 11/2007 |
| WO | WO 2007/139898 A2 | 12/2007 |
| WO | WO 2007/139982 A2 | 12/2007 |

OTHER PUBLICATIONS

Doyon, et al., "Heritable Targeted Gene Disruption in Zebrafish Using Designed Zinc-Finger Nucleases," *Nature Biotechnology* 26:702-708 (2008).

Dujon, et al., "Mobile Introns: Definition of Terms and Recommended Nomenclature," *Gene* 82:115-118 (1989).

Durai, el al., "Zinc Finger Nucleases: Custom-Designed Molecular Scissors for Genome Engineering of Plant and Mammalian Cells," *Nucleic Acids Research* 33(1):5978-5990 (2005).

Epinat, et al., "A Novel Engineered Meganuclease Induces Homologous Recombination in Yeast and Mammalian Cells," *Nucl Acids Res* 31:2952-3965 (2003).

Gimble, et al., "Substrate Recognition and Induced DNA Distortion by the PI-SCEI Endonuclease, an Enzyme Generated by Protein Splicing," *J Mol Biol* 263:163-180 (1996).

Holliday, et al., "The Induction of Mitotic Recombination by Mitomycin C in Ustilago and *Saccharomyces*," *Genetics* 50:323-335 (1964).

Isalan et al., "A Rapid, Generally Applicable Method to Engineer Zinc Fingers Illustrated by Targeting the HIV-1 Promoter," *Nat Biotechnol* 19:656-660 (2001).

Jasin, "Genetic Manipulation of Genomes With Rare-Cutting Endonucleases," *Trends Genet* 12:224-228 (1996).

Lee, et al., "Rag Proteins Shepherd Double-Strand Breaks to a Specific Pathway Suppressing Error-Prone Repair, but Rag Nicking Initiates Homologous Recombination," *Cell* 117:171-184 (2004).

Mani, et al., "Design, Engineering, and Characterization of Zinc Finger Nucleases," *Biochem. Biophys. Res. Commun.* 335:447-457 (2005).

McKinnon, et al., "DNA Strand Break Repair and Human Genetic Disease," *Annu Rev Genomics Hum Genet* 8:37-55 (2007).

Meselson, et al., "A General Model for Genetic Recombination," *PNAS USA* 72:358-361 (1975).

Miller, et al., "An Improved Zinc-Finger Nuclease Architecture for Highly Specific Genome Editing," *Nat Biotech* 25:778-785 (2007).

Moehle, et al., "Targeted Gene Addition Into a Specified Location in the Human Genome Using Designed Zinc Finger Nucleases," *PNAS USA* 104:3055-3060 (2007).

Okano, et al., "Spatial and Temporal Cellular Responses to Single-Strand Breaks in Human Cells," *Mol Cell Biol* 23:3974-3981 (2003).

Pabo, et al., "Design and Selection of Novel CYS2-HIS2 Zinc Finger Proteins," *Ann. Rev. Biochem.* 70:313-340 (2001).

Pâques, et al., "Meganucleases and DNA Double-Strand Break-Induced Recombination: Perspectives for Gene Therapy," *Current Gene Therapy* 7:49-66 (2007).

Perler, et al., "Protein Splicing Elements: Inteins and Exteins—A Definition of Terms and Recommended Nomenclature," *Nucl Acids Res* 22:1125-1127 (1994).

Porteus, et al., "Gene Targeting Using Zinc Finger Nucleases," *Nature Biotechnology* 23:967-973 (2005).

Radding, Charles M., "Homologous Pairing and Strand Exchange in Genetic Recombination," *Ann Rev Genet* 16:405-437 (1982).

Segal, et al., "Custom DNA-Binding Proteins Come of Age: Polydactyl Zinc-Finger Proteins," *Curr. Opin. Biotechnol.* 12:632-637 (2001).

Szekvolgyi, et al., "Ribonucleoprotein-Masked Nicks at 50-KBP Intervals in the Eukaryotic Genomic DNA," *PNAS USA* 104:14964-14969 (2007).

Niu, et al., "Engineering Variants of the I-SCEL Homing Ensonuclease With Strand-Specific and Site-Specific DNA Nicking Activity," *J. Mol. Biol.* 382(1):188-202 (2008).

Smith, et al., "Generation of a Nicking Enzyme That Stimulates Lite-Specific Gene Conversion From the I-ANIL Laglidadg Homing Endonuclease," PNAS USA 106(13):5099-5104 (2009).

Wang, et al., "Preparation of DNA Substrates for In Vitro Mismatch Repair," Molecular Biotechnology 97-104 (2000).

\* cited by examiner

US 9,200,266 B2

METHODS AND COMPOSITIONS FOR TARGETED SINGLE-STRANDED CLEAVAGE AND TARGETED INTEGRATION

CROSS-REFERENCE TO RELATED APPLICATIONS

This application is a continuation application of U.S. patent application Ser. No. 12/583,329, filed Aug. 18, 2009, now U.S. Pat. No. 8,703,489, which claims the benefit of U.S. Provisional Application No. 61/189,800, filed Aug. 22, 2008, which is incorporated by reference herein in its entirety.

STATEMENT OF RIGHTS TO INVENTIONS MADE UNDER FEDERALLY SPONSORED RESEARCH

Not applicable.

TECHNICAL FIELD

The present disclosure is in the fields of genome engineering, gene targeting, targeted chromosomal integration and protein expression.

BACKGROUND

A major area of interest in genome biology, especially in light of the determination of the complete nucleotide sequences of a number of genomes, is the targeted alteration of genome sequences.

Artificial nucleases, which link the cleavage domain of nuclease to a designed DNA-binding protein (e.g., zinc-finger protein (ZFP) linked to a nuclease cleavage domain such as from FokI), have been used for targeted cleavage in eukaryotic cells. For example, zinc finger nuclease-mediated genome editing has been shown to modify the sequence of the human genome at a specific location by (1) creation of a double-strand break (DSB) in the genome of a living cell specifically at the target site for the desired modification, and by (2) allowing the natural mechanisms of DNA repair to "heal" this break.

To increase specificity, the cleavage event is induced using one or more pairs of custom-designed zinc finger nucleases that dimerize upon binding DNA to form a catalytically active nuclease complex. In addition, specificity has been further increased by using one or more pairs of zinc finger nucleases (ZFNs) that include engineered cleavage half-domains that cleave double-stranded DNA only upon formation of a heterodimer. See, e.g., U.S. Patent Publication No. 20080131962, incorporated by reference herein in its entirety.

The double-stranded breaks (DSBs) created by artificial nucleases have been used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 20060063231; 20070218528; 20070134796; 20080015164 and International Publication Nos. WO 07/014275 and WO 2007/139982, the disclosures of which are incorporated by reference in their entireties for all purposes. Thus, the ability to generate a DSB at a target genomic location allows for genomic editing of any genome.

There are two major and distinct pathways to repair DSBs—homologous recombination and non-homologous end joining (NHEJ). Homologous recombination requires the presence of a homologous sequence as a template (e.g., "donor") to guide the cellular repair process and the results of the repair are error-free and predictable. In the absence of a template (or "donor") sequence for homologous recombination, the cell typically attempts to repair the DSB via the unpredictable and error-prone process of non-homologous end joining (NHEJ).

Single strand breaks (SSBs), including DNA nicks, are one of the most frequent DNA lesions produced by endogenous reactive oxygen species and during DNA metabolism, such as DNA repair and replication. See, McKinnon et al. (2007) *Annu Rev Genomics Hum Genet.* 8:37-55; Okano et al. (2003) *Mol Cell Biol* 23:3974-3981. Chromosomes of non-apoptotic cells contain single-strand discontinuities (SSBs/nicks) positioned at about 50 kb intervals all over the entire genome. See, e.g., Szekvolgyi et al. (2007) *Proc Natl Acad Sci USA* 104: 14964-14969. Most SSB/nicks are repaired by a rapid global SSB repair process that can be divided into four basic steps: SSB detection by poly (ADP-ribose) polymerase-1 (PARP-1), DNA end processing by various enzymes, DNA gap filling by DNA polymerases, and DNA ligation by DNA ligases, See Caldecott, K. W. (2008) *Nat Rev Genet.* 9, 619-31. Lee et al. (2004) *Cell* 117:171-184 found data to suggest that nicks induced by mutated RAG proteins might initiate homology-directed repair (HDR) in mammalian cells.

However, it has not previously been shown that ZFNs can be engineered to induce SSBs/nicks, or that these SSBs/nicks can be repaired by homologous recombination, or that they can be used to facilitate the targeted integration of a transgene via homologous recombination. Thus, there remains a need for methods and composition that generate single-stranded breaks (nicks) in double-stranded DNA and facilitate targeted integration by homologous recombination at the nicked site, without simultaneously occurrence of error-prone NHEJ repair in mammalian/human cells.

SUMMARY

Disclosed herein are methods and compositions for inducing a targeted single-stranded break in any double-stranded target sequence of interest. Also described are methods of facilitating homologous recombination and targeted integration following single-stranded cleavage of a target. Thus, targeted modulation of a genome is described.

In one aspect, artificial (non-naturally occurring) nucleases that generate single-stranded cuts in a desired double-stranded target sequence are provided. The nucleases described herein comprise a DNA-binding domain (e.g., engineered zinc finger protein) and at least one cleavage domain or at least one cleavage half-domain In certain embodiments, the nucleases are zinc finger nucleases comprising a zinc finger domain that is engineered to bind any selected sequence (e.g., gene). Any of the zinc finger proteins described herein may include 1, 2, 3, 4, 5, 6 or more zinc fingers, each zinc finger having a recognition helix that binds to a target subsite in the selected sequence(s) (e.g., gene(s)). The cleavage domain can be derived from any nuclease, for example, a cleavage half-domain from a Type IIS nuclease, such as FokI. In certain embodiments, the cleavage half-domain comprises an engineered FokI cleavage-half domain that forms a heterodimer with another cleavage half-domain (e.g., engineered or wild-type in the dimerization domain). In still further embodiments, the cleavage domain (e.g., engineered FokI cleavage half-domain) comprises a mutation that inactivates the catalytic domain (enzymatic activity) of the nuclease domain In another aspect, provided herein are complexes and/or compositions comprising a pair of zinc finger nucleases, each nuclease comprising an engineered zinc finger domain and a FokI cleavage half-domain, wherein the cleavage half-domain forms a dimer (homodimer or heterodimer). In certain embodiments, one zinc finger nuclease of the pair comprises a first catalytically active engineered cleavage-half domain and the other zinc finger nuclease comprises a second catalytically inactive engineered cleavage half-domain, in which the first and second engineered cleavage half-domains form an obligate heterodimer.

In yet another aspect, a polynucleotide encoding any of the nucleases described herein is provided.

In yet another aspect also provided is an isolated cell comprising any of the proteins and/or polynucleotides described herein. In certain embodiments, cell lines in which exogenous sequences have been introduced via targeted alteration are provided. In certain embodiments, one or more selected gene(s) are inactivated (partially or completely) in these cell lines. In other embodiments, the cells or cell lines include one or more transcribed and/or translated exogenous sequences that have been stably or transiently introduced into the cells. Such cell lines are generated by culturing of cells comprising any of the proteins and/or polynucleotides described herein in a cell line resulting in the inactivation of selected gene(s).

Also provided are transgenic organisms comprising one or more transcribed and/or translated exogenous sequences that have been stably or transiently introduced into the cells. Further provided are transgenic organisms that contain gene(s) selectively inactivated by the methods provided herein, or organisms containing exogenous sequences capable of altering the expression of endogenous sequences. Transgenic organisms as described herein may be plants (e.g. crop plants or tobacco strains) or animals (e.g. mice, rats, rabbits, fish, etc.). In certain embodiments, the transgenic organisms are used to generate lines of organisms carrying one or more sequences encoding nucleases as described herein and/or one or more exogenous sequences (e.g., sequences inserted into the genome via targeted integration using nucleases as described herein). For instance, disclosed herein are transgenic plants and plant lines comprising nucleases as described herein under the control of an inducible promoter. Accordingly, transgenic plants and plant lines comprising episomal or integrated sequences encoding nucleases can be expressed in the plant at the desired time and/or in the desired tissue of the plant.

In addition, methods of generating a specific single-stranded break in a target double-stranded sequence in a cell are provided. In certain embodiments, the methods involve introducing one or more pairs of nucleases (proteins or polynucleotide(s) encoding the nucleases) into the cell. Each nuclease pair comprises a first nuclease with a first DNA-binding domain and a first catalytically active cleavage-half domain and a second nuclease with a second DNA-binding domain and second catalytically inactive cleavage-half domain. The one or more pairs of nucleases are introduced into the cells under conditions such that the first and second cleavage half-domains of each pair form a dimer and generate a single-stranded break in the target sequence.

In certain embodiments, the first and/or second DNA-binding domains comprise a zinc finger protein (e.g., an engineered zinc finger protein). Furthermore, in any of the methods described herein, the first and second cleavage half-domains can comprise FokI cleavage half-domains, for example FokI cleavage half-domains that are engineered to form obligate heterodimers. The target sequence can be any double-stranded sequence, for example, a sequence in cellular chromatin such as a genomic sequence or portion thereof. In addition, the target sequence can be an extrachromosomal double stranded DNA sequence, for example in a plasmid or virus. Similarly, the target sequence can be in any cell type including, prokaryotic and eukaryotic cells, such as fungal cells, plant cells, animal cells, mammalian cells, primate cells and human cells.

The site of single-stranded break can be coincident with the sequence to which the catalytically active nuclease binds, or it can be adjacent (e.g., separated from the near edge of the binding site by 1, 2, 3, 4, 5, 6, 7, 8, 9, 10, 11, 12, 13, 14, 15 or more nucleotides). The fusion proteins can be expressed in a cell, e.g., by delivering the fusion proteins to the cell and/or by delivering a polynucleotide encoding one or more nucleases to a cell, wherein the polynucleotide, if DNA, is transcribed into mRNA which is then translated into the fusion protein. Alternatively, an RNA molecule can be delivered to the cell which then is translated to generate the fusion protein. Methods for polynucleotide and polypeptide delivery to cells are presented elsewhere in this disclosure.

Methods for targeted recombination (for, e.g., alteration or replacement of a sequence in a chromosome or a region of interest in cellular chromatin) are also provided. For example, a mutant genomic sequence can be replaced by a wild-type sequence, e.g., for treatment of genetic disease or inherited disorders. In addition, a wild-type genomic sequence can be replaced by a mutant sequence, e.g., to prevent function of an oncogene product or a product of a gene involved in an inappropriate inflammatory response. Furthermore, one or more alleles of a gene can be replaced by one or more different alleles (e.g., biallelic targeted integration).

In the methods of the disclosure, one or more targeted nucleases as described herein create a single-stranded break in the target sequence (e.g., cellular chromatin) at a predetermined site, and a "donor" polynucleotide, having homology to the nucleotide sequence in the region of the break, can be introduced into the cell. The presence of the single-stranded break has been shown herein to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In addition, a method for replacement of a region of interest in cellular chromatin (e.g., a genomic sequence) with a first nucleotide sequence is provided, the method comprising: (a) engineering a first zinc finger binding domain to bind to a second sequence in the region of interest; (b) providing a second zinc finger binding domain to bind to a third sequence in the region of interest; (c) expressing a first fusion protein in a cell, the first fusion protein comprising the first zinc finger binding domain and a first catalytically active cleavage half-domain; (d) expressing a second fusion protein in the cell, the second fusion protein comprising the second zinc finger binding domain and a second catalytically inactive cleavage half-domain; and (e) contacting the cell with a polynucleotide comprising the first nucleotide sequence; wherein the first fusion protein binds to the second sequence and the second fusion protein binds to the third sequence, thereby positioning the cleavage half-domains such that a single-stranded break is made in cellular chromatin in the region of interest and a nucleotide sequence in the region of interest is replaced with the first nucleotide sequence. In certain embodiments, the single-stranded break in cellular chromatin is made in the region of interest at a site between the second and third sequences. The zinc finger nucleases may be provided to the cells as proteins and/or as one or more polynucleotides encoding said zinc finger nuclease(s). For example, two polynucleotides, each comprising sequences encoding one of the two fusion proteins, can be introduced into a cell. Alternatively, a single polynucleotide comprising sequences encoding both fusion proteins can be introduced into the cell.

In any of the methods described herein, additional pairs of zinc finger proteins can be used for additional double-stranded and/or single-stranded cleavage of additional target sites within the cell.

Thus, in one embodiment, a method for replacement of a region of interest in cellular chromatin (e.g., a genomic sequence) with a first nucleotide sequence comprises: (a) engineering a first zinc finger binding domain to bind to a second sequence in the region of interest; (b) providing a second zinc finger binding domain to bind to a third sequence; and (c) contacting a cell with: (i) a first polynucleotide comprising the first nucleotide sequence; (ii) a second polynucleotide encoding a first fusion protein, the first fusion protein comprising the first zinc finger binding domain and a first catalytically active cleavage half-domain; and (iii) a third polynucleotide encoding a second fusion protein, the second fusion protein comprising the second zinc finger binding domain and a second catalytically inactive cleavage half-domain; wherein the first and second fusion proteins are expressed, the first fusion protein binds to the second sequence and the second fusion protein binds to the third sequence, thereby positioning the cleavage half-domains such that a single-stranded break is generated in cellular chromatin in the region of interest; and the region of interest is replaced with the first nucleotide sequence.

In the preferred embodiments of methods for targeted recombination and/or replacement and/or alteration of a sequence in a region of interest in cellular chromatin, a chromosomal sequence is altered, by homologous recombination with an exogenous "donor" nucleotide sequence. Such homologous recombination is stimulated by the presence of a single-stranded break in cellular chromatin, if sequences homologous to the region of the break are present. Notably, single-strand breaks in cellular chromatin do not stimulate cellular mechanisms of non-homologous end joining.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, for example sequences such as those found in artificial chromosomes, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided. Further still, the plant cell lines with partially or completely inactivated genes can be used to generate transgenic plants. Plant cell lines comprising nucleases as described herein, wherein expression of the nuclease is driven by an inducible promoter are also provided. Similarly, mammalian germ cells, such as oocytes, with partially or completely inactivated genes can be used to generate transgenic animals.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In any of the cells, cell lines and methods described herein, the cell or cell line can be a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), PerC.6® (Crucell); EBx™ (Sigma-Aldrich Group), insect cells such as *Spodoptera fugiperda* (Sf), or fungal cells such as *Saccharomyces*, *Pichia* and *Schizosaccharomyces*.

In another aspect, the invention provides kits comprising one or more nucleases (or polynucleotides encoding these nucleases) as described herein for carrying out the methods as described herein. The kits may optionally comprise reagents, buffers, cells, suitable containers and written instructions.

These and other aspects will be readily apparent to the skilled artisan in light of disclosure as a whole.

BRIEF DESCRIPTION OF THE DRAWINGS

FIG. 2, panels A to C, depict single-stranded cleavage of a double-stranded target using a pair of zinc finger nucleases where one nuclease includes a cleavage domain that has been mutated to inactivate cleavage activity of the nuclease domain.

FIG. 4, panels A to D, depict analysis of non-homologous end joining (NHEJ) and targeted integration (TI) of an exogenous sequence (patch donor) following the induction of double-stranded or single-stranded breaks in the target gene.

FIG. 5, panels A and B, depict analysis of targeted integration and NHEJ in K562 cells transfected with the indicated ZFN combinations in the presence of a 46 bp CCR5-patch donor.

FIG. 6, panels A and B, depict analysis of targeted integration and NHEJ in K562 cells transfected with indicated ZFN combinations in the presence of a CCR5-tNGFR-outGFP donor.

DETAILED DESCRIPTION

Figure 1:
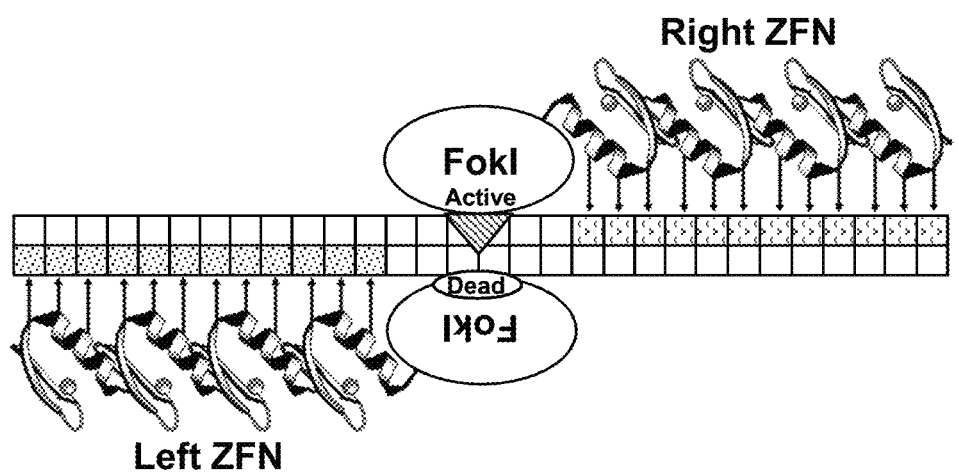
FIG. 1 is a schematic depicting an exemplary zinc finger nuclease (ZFN) architecture that includes an inactivated cleavage domain. The ZFN pair cleaves only one DNA strand to form single-stranded breaks (SSBs), also referred to as nicks.

Disclosed herein are compositions and methods useful for targeted single-stranded cleavage of cellular chromatin and for targeted alteration of a cellular nucleotide sequence, e.g., by targeted single-stranded cleavage followed by homologous recombination between an exogenous polynucleotide (comprising one or more regions of homology with the cellular nucleotide sequence) and a genomic sequence. Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, translocations, rearrangements, and/or point mutations. A genomic sequence can also comprise one of a number of different alleles. The compositions and methods can also be used for targeted alteration of extrachromosomal nucleotide sequences, e.g. plasmids.

Compositions useful for targeted single-stranded cleavage and recombination include fusion proteins comprising a cleavage half-domain and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any genomic or episomal sequence. Thus, by identifying a target genomic or episomal region of interest at which cleavage or recombination is desired, one can, according to the methods disclosed herein, construct one or more fusion proteins comprising both a catalytically active and catalytically inactive cleavage half-domain and a zinc finger domain engineered to recognize a target sequence in said genomic or episomal region. The presence of such a fusion protein (or proteins) in a cell will result in binding of the fusion protein(s) to its (their) binding site(s) and single-stranded cleavage within or near said genomic or episomal region. Notably, as shown herein, if an exogenous polynucleotide having regions homologous to the genomic or episomal region is also present in such a cell, homologous recombination occurs at a high rate between the genomic or episomal region and the exogenous polynucleotide.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P.M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Therefore, engineered zinc finger proteins are proteins that are non-naturally occurring. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length. Alternately, a donor sequence can be an artificial chromosome sequence such as a bacterial artificial chromosome (BAC) or yeast artificial chromosome (YAC).

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides, an artificial chromosome, or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acids, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

Conditions for hybridization are well-known to those of skill in the art (see, for example, *Nucleic Acid Hybridization: A Practical Approach*, editors B. D. Hames and S. J. Higgins, (1985) Oxford; Washington, D.C.; IRL Press). Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized faun of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Single-stranded cleavage refers to cleavage of one stand of double-stranded DNA/RNA and double-stranded cleavage refers to cleavage of both strands (e.g., via two distinct single-stranded cleavage events). In certain embodiments, fusion polypeptides are used for targeted single-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain) See, also, U.S. Patent Publication Nos. 2005/0064474; 2007/0218528; 2008/0131962 and U.S. patent application Ser. No. 12/217,185, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form) of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequenced may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and one or more cleavage domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be complete (knock-out) or partial (e.g., a hypomorph in which a gene exhibits less than normal expression levels or a product of a mutant gene that shows partial reduction in the activity it influences).

"Eukaryotic" cells include, but are not limited to, fungal cells (such as yeast), plant cells, animal cells, mammalian cells and human cells (e.g., T-cells).

A "cell line" refers to a population of cells established in tissue culture from a primary culture. Thus, cell lines generated using zinc finger nuclease(s) arise from a cell (or cell line) in which one or more target genes have been partially or completely inactivated by one or more zinc finger nucleases and in which the progeny of the cell (or cell line) retain the partial or complete inactivation phenotype after multiple passages in culture. Furthermore, a cell or cell line is "deficient" in expression of one or more indicated genes when expression of the gene(s) is(are) reduced (knock-downs) or eliminated (knockouts).

By "transgenic" is meant any animal or plant which includes a nucleic acid sequence which is introduced into a cell and becomes part of the genome of the animal or plant. The term refers to a genetically engineered animal or plant as well as offspring of genetically engineered animals. The non-human transgenic animal includes vertebrates such as rodents, non-human primates, sheep, dogs, cows, amphibians, birds, fish, insects, reptiles, etc. The term also includes animals and plants in which the introduced nucleic acid sequence is found, or in which the nucleic acid sequence gene is expressed, in some but not all cells of the animal or plant.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

The term "antibody" as used herein includes antibodies obtained from both polyclonal and monoclonal preparations, as well as, the following: hybrid (chimeric) antibody molecules (see, for example, Winter et al., Nature (1991) 349: 293-299; and U.S. Pat. No. 4,816,567); F(ab')2 and F(ab) fragments; Fv molecules (non-covalent heterodimers, see, for example, Inbar et al., Proc Natl Acad Sci USA (1972) 69:2659-2662; and Ehrlich et al., Biochem (1980) 19:4091-4096); single-chain Fv molecules (sFv) (see, for example, Huston et al., Proc Natl Acad Sci USA (1988) 85:5879-5883); dimeric and trimeric antibody fragment constructs; minibodies (see, e.g., Pack et al., Biochem (1992) 31:1579-1584; Cumber et al., J Immunology (1992) 149B: 120-126); humanized antibody molecules (see, for example, Riechmann et al., Nature (1988) 332:323-327; Verhoeyan et al., Science (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

Nucleases

Described herein are artificial nucleases that can be used to make single-stranded breaks (SSBs, also referred to as "nicks") in double-stranded DNA. Also described herein are methods of facilitating homologous recombination (e.g., targeted integration) by introducing a SSB into the genome.

A. Cleavage Domains

The nucleases described herein comprise a nuclease (cleavage domain, cleavage half-domain) The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains. For example, the cleavage domain of a meganuclease such as SceI can be rendered partially inactive to induce SSBs rather than DSBs.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Nat'l. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

For example, in certain embodiments, nuclease combinations are used in which the cleavage domains have a mutation at 490 that replaces Glu (E) with Lys (K); a mutation at 538 that replaces Iso (I) with Lys (K); a mutation at 486 that replaces Gln (Q) with Glu (E); and a mutation at position 499 that replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" or "KK" and by mutating positions 486 (Q→E) and 499 (I→L) in another cleavage half-domain to produce an engineered cleavage half-domain designated "Q486E:I499L" or "EL."

Another example of a pair of engineered cleavage half-domains that form an obligate heterodimer (in which aberrant cleavage is minimized or abolished) is one in which one cleavage half-domain is mutated at position 487 (R→D, also referred to as "RD") and other cleavage half-domain is mutated at position 483 (D→R, also referred to as "DR").

Engineered cleavage half-domains described herein can be prepared using any suitable method, for example, by site-directed mutagenesis of wild-type cleavage half-domains (Fok I) as described in U.S. Patent Publication No. 20050064474 (see, e.g., Example 5); and WO 07/139,898.

The cleavage half-domains of the present invention may also include one more mutations the catalytic domain of the nuclease, which renders the cleavage half-domain inactive. Non-limiting examples of amino acids that can be mutated in the catalytic domain of FokI includes amino acid residues 450, 467 and/or 469 (as determined relative to wild-type). In certain embodiments, one or more point mutations are made in the catalytic domain of one member of the obligate heterodimer so as to inactivate the catalytic activity of the cleavage half-domain. For instance, position 450 may be mutated from D to N, position 467 may be mutated from D to A; and position 469 may be mutated from K to A. Other amino acids may be substituted at these or other positions.

B. DNA-binding Domains

The nucleases described herein also comprise at least one DNA-binding domain. Any DNA-binding domain can be used in the compositions and methods disclosed herein. In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In certain embodiments, the nucleases as described herein comprise one DNA-binding domain and one cleavage domain, for example a zinc finger protein and a FokI cleavage half-domain. In other embodiments, the nuclease comprises one DNA-binding domain and two or more cleavage domains, for example a zinc finger protein comprising one catalytically active FokI cleavage half-domain and one catalytically inactivate FokI cleavage half-domain. The cleavage half-domains are able to dimerize when the DNA-binding domain is bound to its target site and produce a single-stranded cut near the target site.

Delivery

The nucleases (e.g., ZFNs) described herein may be delivered to a target cell by any suitable means. Suitable cells include but not limited to eukaryotic (animal and/or plant) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces*, *Pichia* and *Schizosaccharomyces*. In certain embodiments, the cell line is a CHO-K1, MDCK or HEK293 cell line. In addition, primary cells which may be sensitive to double strand breaks may be used. These may include, but are not limited to, CD34+ human stem cells, embryonic stem cells, mouse embryonic stem cells, and induced pluripotent cells. Cells known to be used in the creation of transgenic organisms, such as mouse embryonic stem cells and oocytes may also be used.

Methods of delivering nucleases comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases as described herein may also be delivered using vectors containing sequences encoding one or more of the nuclease(s) (e.g., ZFNs). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties, also described in detail constitutive or inducible promoters that can be operably linked to the sequences encoding the nuclease(s) to drive expression of these nucleases. Furthermore, it will be apparent that any of these vectors may comprise one or more nuclease encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946, 787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, PNAS 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used. In addition, primary cells which may be sensitive to double strand breaks may be used. These may include, but are not limited to, CD34+ human stem cells, embryonic stem cells, mouse embryonic stem cells, and induced pluripotent cells. Cells known to be used in the creation of transgenic organisms, such as mouse embryonic stem cells and oocytes may also be used.

Applications

The disclosed compositions and methods can be used for any application in which introduction of a single-stranded break at a selected location is desired. Moreover, as demonstrated herein, single-stranded cleavage facilitates targeted integration into the site of the single-stranded break (via homologous recombination), without inducing non-homologous end-joining (NHEJ) events.

Thus, the compositions and methods described herein can be used for any nuclease application in which specifically targeted single-stranded cleavage is desirable and/or to replace any genomic sequence with an exogenous sequence (e.g., homologous, non-identical sequence).

For targeted integration, one or more zinc finger binding domains are engineered to bind a target site at or near the predetermined cleavage site, and a fusion protein comprising the engineered zinc finger binding domain(s) and at least first and second cleavage half-domains (that form a dimer) are expressed in a cell. The first cleavage domain is catalytically inactivated and, upon binding of the zinc finger portion of the fusion protein to the target site and dimerization of the cleavage half-domains, a single-stranded cut is made in the DNA near the target site.

The presence of a single-stranded break facilitates integration of exogenous sequences via homologous recombination. Thus, a polynucleotide comprising at least one exogenous sequence to be inserted into the genome will typically include one or more regions of homology with target gene to facilitate homologous recombination.

Any sequence of interest (exogenous sequence) can be introduced as described herein. Exemplary exogenous sequences include, but are not limited to any polypeptide coding sequence (e.g., cDNAs), promoter, enhancer and other regulatory sequences, shRNA expression cassettes, epitope tags, marker genes, cleavage enzyme recognition sites and various types of expression constructs. In addition, the exogenous nucleic acid sequence may produce one or more RNA molecules (e.g., small hairpin RNAs (shRNAs), inhibitory RNAs (RNAis), microRNAs (miRNAs), etc.). Such sequences can be readily obtained using standard molecular biological techniques (cloning, synthesis, etc.) and/or are commercially available. For example, MISSION™ TRC shRNA libraries are commercially available from Sigma Aldrich.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), cell surface antigens (e.g., ΔNGFR) and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs. The exogenous sequence may also encode transcriptional regulatory factors.

For example, the exogenous sequence comprises a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration following single-stranded cleavage include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia,β-thalassemia) and hemophilias.

In certain embodiments, the exogenous sequences can comprise a marker gene (described above), allowing selection of cells that have undergone targeted integration, and a linked sequence encoding an additional functionality.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Nucleases as described herein can also be used for inactivation (partial or complete) of one or more genomic sequences. Inactivation can be achieved, for example, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

ZFN-mediated inactivation (e.g., knockdown or knockout) of endogenous genes can be used, for example, to generate cell lines deficient in genes involved in apoptosis or protein production (e.g., post-translational modifications such as fucosylation). ZFN-mediated inactivation can also be used to generate transgenic organisms (e.g., plants or transgenic animals).

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, International Patent Publication WO 2007/139982. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CD4, CCR-5 and CXCR-4.

The methods and compositions as described herein can also be used in in vitro contexts, for example, as a tool for the introduction of a site-specific nick in an isolated DNA template, for nucleic acid amplification (e.g., for cloning, library production), for nucleic acid detection in any sample (e.g., diagnostics of the presence of genetic conditions and/or infectious agents), for genome walking, for analysis of DNA methylation analysis and the like. See, e.g., U.S. Pat. Nos. 7,314,714; 7,112,423; 7,090,804; 6,884,586; and 6,395,523. For instance, nicking nucleases as described herein can be used alone or in combination with other enzymes to generate long and non-complementary overhangs as well as other structures.

In addition, the compositions as described herein can be used for generation of nicked (or gapped) double stranded DNA for stand displacement amplification (SDA), an isothermal DNA amplification approach that provides a rapid (as short as 15 minutes) alternative to detection of polymerase chain reaction (PCR). See, e.g., U.S. Pat. No. 5,523,204; Walker et al. (1992) Nucleic Acids Res. 20(7): 1691-1696. The use of SDA to date has depended on modified phosphorthioate nucleotides in order to produce a hemi-phosphorthioate DNA duplex that on the modified strand would be resistant to enzyme cleavage, resulting in enzymatic nicking instead of digestion to drive the displacement reaction or on engineered "nickase" enzymes that do not cut double-stranded DNA. Accordingly, the nucleases described herein can be readily adapted for any application in which SDA is currently applied. Thus, the compositions of the invention can be used in detection of nucleic acid sequences and, accordingly, in the diagnosis of the presence of genetic diseases and/or infectious agents, such as HPV, Hepatitis virus (HCV, HBV, HAV), HIV, *Mycobacterium tuberculosis* and *Chlamydia trachomatis*, from any sample (e.g., blood, urine, plasma, tissue samples, isolated cells, fixed cells, etc.).

Additional in vitro applications include the generation of exonucleolytic degradations. For example, nicking nucleases as described herein can be used in combination with S1 for the creation of nested deletions. See, e.g., U.S. Pat. Nos. 7,244, 560; 6,867,028; and 6,828,098.

EXAMPLES

Example 1

Design and Construction of ZFNs with Mutant Cleavage Domains

Zinc finger proteins targeted to CCR5 as described in International Patent Publication No. WO 2007/139982 were operably linked to engineered cleavage domains as described in U.S. Patent Publication No. 2008/0131962, essentially as described in U.S. Patent Publication No. 20050064474 and International Patent Publication WO2005/014791.

Specifically, CCR5-binding zinc finger protein designated 8196z was fused to either the obligate heterodimer forming cleavage domain having (1) E490K and I538K mutations to form the zinc finger nuclease (ZFN) designated "8196zKK" or (2) an D483R mutation to produce the ZFN designated "8196zDR." Similarly, the CCR5-binding zinc finger protein designated 8267 was fused to either the obligate heterodimer forming cleavage domain having (1) Q486E and I499L mutations to form the ZFN designated "8267EL" or (2) an R487D mutation to form the ZFN designated "8267RD." Catalytically inactive forms of all four ZFNs were also prepared by site-directed mutagenesis of amino acid residues 450 (D to N, designated D450N); 467 (D to A, designated D467A); or 469 (K to A, designated K469A).

Example 2

Dimers of Cleavage Domains with One Catalytically Inactive Cleavage Domain Induce Single-stranded Breaks The ZFNs described in Example 1 were used in various pairwise combinations and cleavage events evaluated. In particular, ZFN variants described in Example 1 were synthesized using TNT T7 Quick™ coupled transcription/translation system (Promega).

The appropriate substrate containing the ZFNs target sites was generated by PCR amplification of CCR5 sequences flanking CCR5ZFN binding region to generate a 292 base pair substrate. The substrates were $^{32}$P end-labeled using T4 polynucleotide kinase and incubated with the following ZFN pairs: 8196zKK and 8267EL (WT); 8196zKK and 8267EL, where 8267 EL includes catalytically inactivating point mutation D450N (D450N); 8196zKK and 8267EL, where 8267 EL includes catalytically inactivating point mutation D467A (D467A); 8267RD and 8196zDR (WT); 8267RD and 8196zDR, where 8196zDR includes catalytically inactivating point mutation D450N (D450N); and 8267RD and 8196zDR, where 8196zDR includes catalytically inactivating point mutation D467A (D467A). The mixture of radio-labeled substrate DNA and ZFN proteins was incubated at 37° C. for 2 hr as described previously (Miller et al (2007) Nat. Biotech. 25:778-785) with modifications described below.

Cleaved DNA were extracted by phenol/chloroform and either untreated (double-stranded cleavage products) or treated with a DNA denaturing solution (1.0M glyoxal, 10 mM $NaH_2PO_4/Na_2HPO_4$, pH 7.0, 50% DMSO) to generate single-stranded DNA before separation on a 10% Ready™ gel TBE gel (Invitrogen).

Figure 2A:
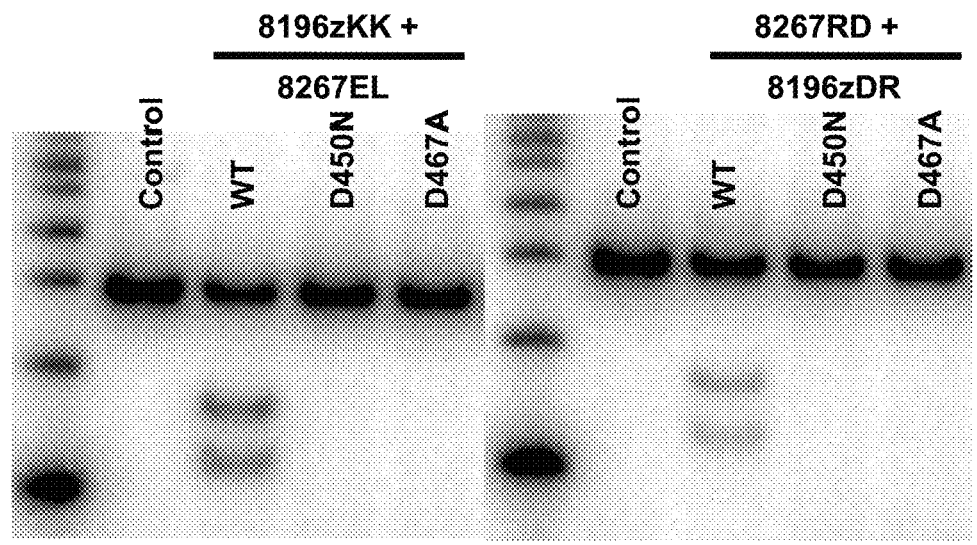
FIG. 2A depicts analysis of double-stranded cleavage products obtained by cleavage of a target substrate with the indicated ZFN pairs. From left to right, lanes show: molecular weight ladder, control, a CCR5-targeted ZFN pair designated 8196zKK:8267EL, where KK and EL refer to engineered cleavage domains that form obligate heterodimers to generate double-stranded breaks (see, U.S. Patent Publication 2008/0131962), referred to as wildtype 8196zKK8267EL (WT) in this application; a CCR5-targeted ZFN pair designated 8196zKK:8267EL, where the 8267EL protein also contains a mutation at position 450 of the catalytic domain (D450N) of one cleavage half-domain that inactivates one cleavage half-domain of the ZFN pair; a CCR5-targeted ZFN pair designated 8196zKK:8267EL, where the 8267EL protein also contains a mutation at position 467 in the catalytic domain (D467A) that inactivates one cleavage half-domain of the ZFN pair; a second molecular weight ladder, a second control; a CCR5-targeted ZFN pair designated 8267RD:8196zDR, where RD and DR refer to engineered cleavage domains that form obligate heterodimers (see, U.S. Patent Publication 2008/0131962), referred to as wildtype 8267RD:8196zDR (WT) in this application; a CCR5-targeted ZFN pair designated 8267RD:8196zDR, where the 8196zDR protein also contains a mutation at position 450 of the catalytic domain (D450N) of one cleavage half-domain that inactivates one cleavage half-domain of the ZFN pair; a CCR5-targeted ZFN pair designated 8267RD:8196zDR, where the 8196zDR protein also contains a mutation at position 467 in the catalytic domain (D467A) that inactivates one cleavage half-domain of the ZFN pair.

As shown in FIG. 2A, double-stranded cleavage products were efficiently generated only with ZFN pairs 8196zKK+ 8267EL (WT) or 8267RD+8196zDR (WT), in which the FokI cleavage half-domains of both left and right ZFNs are catalytically active. The parental uncut DNA (292 bp) is present with all ZFN pairs. Two fragments (~168 bp and ~124 bp) were seen with when both ZFNs were catalytically active (8196zKK+8267EL (WT) or 8267RD+8196zDR (WT) pairs). For all ZFN pair combination in which one of the ZFNs is catalytically inactivated by the indicated point mutation, double-stranded breaks in the CCR5 target DNA were not generated.

Figure 2B:
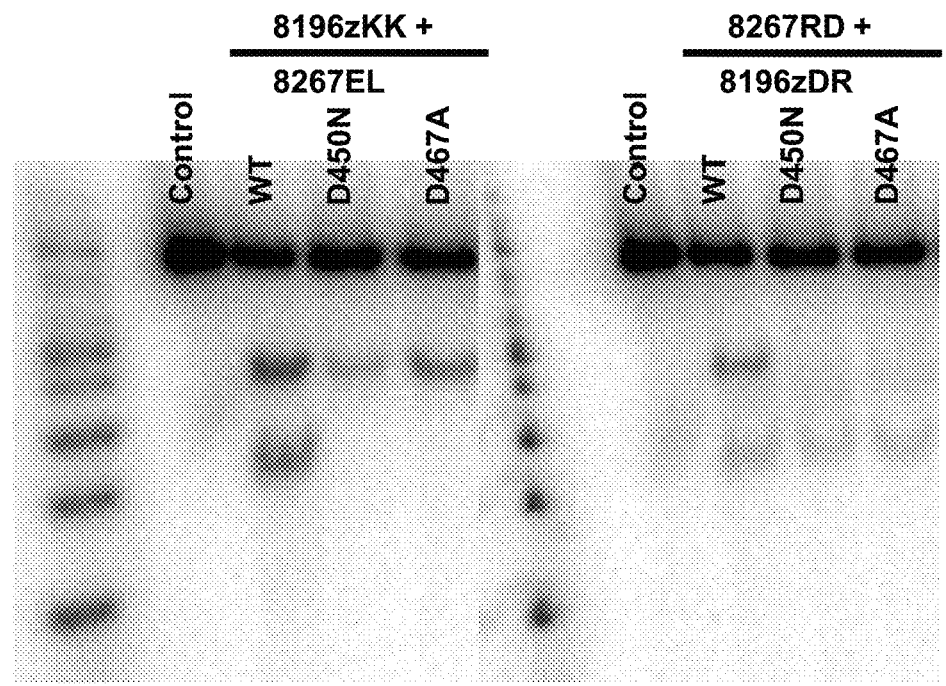
FIG. 2B depicts analysis of single-stranded cleavage products obtained by cleavage of a target substrate with the indicated ZFN pairs. As described above for FIG. 2A, from left to right, lanes show: molecular weight ladder, control, a CCR5-targeted ZFN pair designated 8196zKK:8267EL(WT); the CCR5-targeted ZFN pair designated 8196zKK:8267EL (D450N); the CCR5-targeted ZFN pair designated 8196zKK:8267EL(D467A); a second molecular weight ladder, a second control; the CCR5-targeted ZFN pair designated 8267RD:8196zDR (WT); the CCR5-targeted ZFN pair designated 8267RD:8196zDR (D450N); and the CCR5-targeted ZFN pair designated 8267RD:8196zDR (D467A).
Figure 2C:
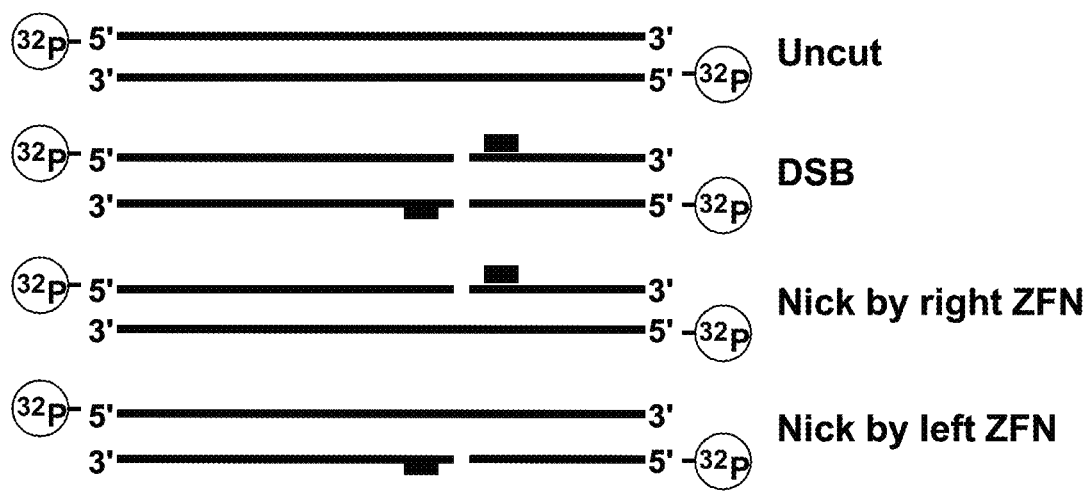
FIG. 2C is a schematic depicting possible cleavage patterns using mutant cleavage domains as described herein, showing which bands will be detected in the autoradiographical analysis due to the position of the radiolabel on the various DNA segments.

However, as shown in FIG. 2B, ZFN pairs with one catalytically inactive ZFN induced single-stranded breaks. In particular, the ~168 bp fragment seen when both FokI cleavage half-domains are catalytically active in double-stranded cleavage products (FIG. 2A, lanes 3 and 8 from left) was also seen in single-stranded cleavage products treated with ZFN pairs 8196zKK+8267EL D450N and 8196zKK+8267EL D467A (containing one catalytically inactive cleavage domain) See, FIG. 2B, lanes 4 and 5 from left. The smaller ~124 bp fragment is not visible because only the 5' end of each DNA strand was end-labeled (see, FIG. 2C).

Similarly, the ~124 bp fragment seen when both FokI cleavage half-domains are catalytically active in double-stranded cleavage products (FIG. 2A, lanes 3 and 8 from left) was also seen in single-stranded cleavage products treated with 8267RD+8196zDR D450N or 8267RD+8196zDR D467A (each containing a catalytically inactive cleavage half-domain). See, FIG. 2B, lanes 9 and 10 from left. Again, the larger ~168 bp fragment is not visible in these samples because only the 5' end of each DNA strand was end-labeled (see, FIG. 2C).

These results demonstrate that the use of dimers of cleavage half-domains in which one cleavage half-domain is catalytically inactivated generates SSBs/nicks in double-stranded DNA.

Example 3

Repairing SSB/Nicks by Single-strand Annealing in Cells

A. Yeast cells

To evaluate whether SSB/nicks can be used as an alternative method for inducing recombination-based genome editing at a targeted locus, we first tested the system in yeast, essentially as described in Doyon et al. (2008) Nat Biotechnol 26:702-8 and U.S. Patent Publication No. 20090111119.

A SSA-MEL1 reporter yeast strain, in which the CCR5ZFN-targeting sites was introduced between the 2 overlapping and nonfunctional fragments of MEL1 gene, was transformed with the ZFN expression plasmids: ZFN-L-EL-D450N+ZFN-R-KK (D450N), ZFN-L-EL-D467A+ZFN-R-KK (D467A) or control vectors (Control). ZFN expression was induced by culture cells in 2% galactose for 2 to 6 hours before overnight culturing in glucose media and assaying for galactosidase activity.

Significantly increased galactosidase activities were observed along with the induction of ZFN expression for 2-6 hours by galactose in cultures treated with D450N/WT (40.0-75.5 mU) or D467A/WT (51.7-96.0 mU) ZFNs compared to cultures treated with the control vectors (2.7-4.1 mU), demonstrating that SSB/nicks induced by ZFNs as described herein are recombinogenic and can be repaired by single-strand annealing in yeast.

To ensure that ZFNs induced MEL1 expression via SSA repair of SSB/nicks and not DSBs, the ability of the ZFNs to induce DSB formation was also evaluated. In the absence of homologous template sequence, DSB induction is lethal to more than 99.8% of the yeast cells in a colony. Yeast cells with the CCR5 ZFN target sites integrated into the HO locus were transformed with ZFN expression plasmids and cultured in minimal media containing glucose or galactose at ten-fold serial dilutions. Only cells in which the ZFNs do not induce DSBs would be expected to survive induction of ZFN expression.

The cells grew well in the presence of glucose (no induction of ZFN expression) regardless of the ZFN expression plasmid introduced in these cells. In the presence of galactose, we observed a 2-3 log reduction in the number of yeast cells that survived in culture when treated with the WT/WT ZFNs, as compared to cultures treated with control vectors. In contrast, yeast transformed with an expression construct replacing one of the WT/WT ZFNs with one of the ZFNs variants (D450N or D467A) were indistinguishable from those cultures treated with the control vectors. Western blot analysis of extracts taken from these cultures confirmed that the expression levels of the ZFN proteins were similar.

As the observed lethality is completely dependent on the presence of the integrated CCR5 target sites, it is not due to the generation of random DSBs by the wild-type ZFN. Therefore, these results confirmed that within the context of a living cell, the ZFNs generating SSB induce SSA-mediated repair via SSB/nick formation and do not catalyze DSBs.

B. Mammalian Cells

To evaluate whether SSB/nicks can be repaired by an HDR-dependent SSA pathway in mammalian cells, K562 cells were co-transfected with ZFN expression plasmids and a SSA-GFP reporter plasmid, in which the eGFP open reading frames with repeated homologous sequences flank a stretch of DNA encoding the CCR5ZFN target sites (required for HDR dependency), and the number of cells undergoing SSA-mediated repair and expressing GFP was then monitored by flow cytometric analysis.

Figures 3A, 3B, 3C, 3D, 3E:
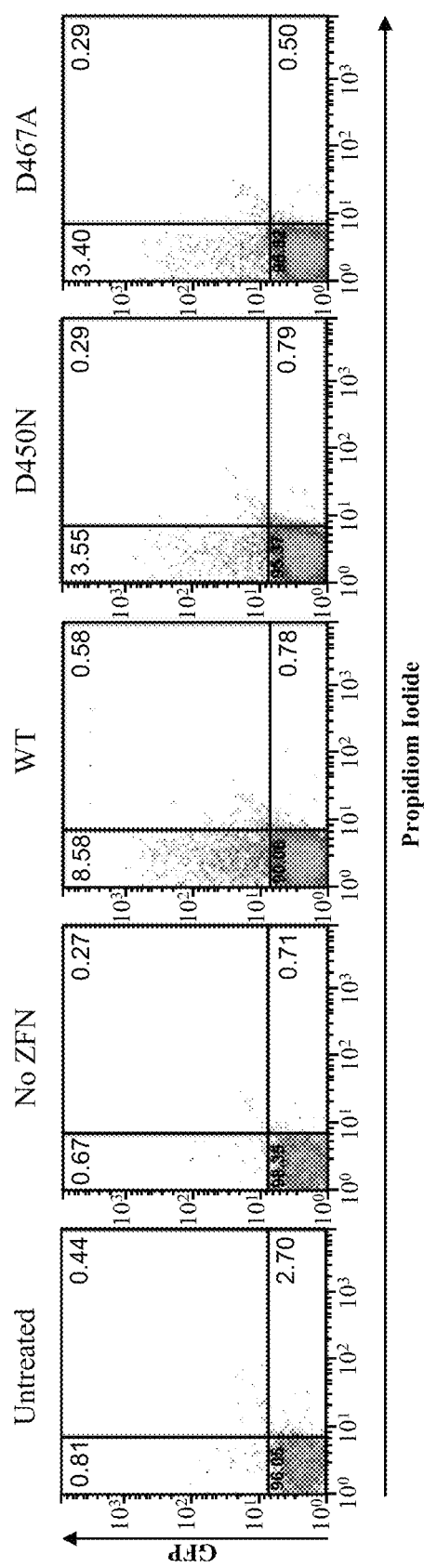
FIG. 3, panels A through E, depict repair of ZFN-induced SSB/nicks in K562 cells by an HDR-dependent single-strand annealing (SSA) pathway. K562 cells were either untreated (Untreated, FIG. 3A) or transfected with a SSA-GFP reporter DNA plasmid in the absence (No ZFN, FIG. 3B) or presence of ZFN expression plasmids as described above in FIG. 2A: the CCR5-targeted ZFN pair designated 8196zKK:8267EL (WT, FIG. 3C); the CCR5-targeted ZFN pair designated 8196zKK:8267EL (D450N, FIG. 3D); the CCR5-targeted ZFN pair designated 8196zKK:8267EL (D467A, FIG. 3E). Cells were collected 3 days post-transfection and subjected to flow cytometric analysis after 5 min incubation with propidium iodide (PI) to stain non-viable cells (PI$^+$). Integration of the GFP donor sequence into the break in the CCR5 gene occurs through an HDR-dependent pathway since the GFP donor sequence is flanked by CCR5 sequences that are homologous to regions flanking the nick site. Thus, an increase in the observed GFP fluorescent signal indicated targeted integration of the donor sequence has occurred. Percentage of cells in each quadrant is indicated at the upper corner of quadrant. The data demonstrate that the ZNF pairs containing the D450N and the D467A mutants are able to integrate the GFP sequences.

As shown in FIG. 3, significantly more GFP$^+$ cells were observed in samples treated with D450N/WT (ZFN-L-EL-D450N+ZFN-R-KK+SSA-GFP reporter, 3.55%) or D467A/WT (ZFN-L-EL-D467A+ZFN-R-KK+CCR5-SSA-GFP reporter, 3.40%) than the sample treated with the SSA-GFP reporter alone (0.67%), though it is 2-3 fold less compared to the sample treated with WT/WT ZFNs (ZFN-L-EL+ZFN-R-KK+SSA-GFP reporter, 8.58%).

These data indicate that SSB/nicks generated by ZFNs generating SSBs can also be repaired by the SSA pathway in mammalian cells.

Example 4

Single-stranded Breaks Facilitate Target Integration by Homologous Recombination The ability of ZFNs that induce SSB/nicks to facilitate homologous recombination and/or NHEJ was also determined.

Briefly, K562 cells were treated with ZFN combinations indicated in Table 1 alone or with ZFN combinations indicated in Table 1 and a CCR5 patch donor sequence. Genomic DNAs were collected from treated cells after 3 days and then tested for NHEJ events by the Surveyor™ nuclease assay and TaqMan™ qPCR assay. In addition, an RFLP assay was used to test targeted integration by homologous recombination.

A. Non-homologous End Joining

As noted above, the percentage of NHEJ events was estimated by Surveyor™ nuclease assay and TaqMan™ qPCR assay. Briefly, the Surveyor™ nuclease assay was conducted as described in Miller et al (2007) *Nat. Biotech.* 25:778-785). The Taqman™ qPCR assay was conducted according to the manufacturer's instruction to measure the presence of a 5 bp insertion known to occur in approximately 10 to 30% of cells following double-stranded cleavage with CCR5ZFNs. Accordingly, specific primers were designed based on this pentamer insertion event, tested, and optimized. The assay is able to detect 1 copy of the plasmid DNA containing the pentamer insertion sequence. The assay can also easily detect 0.01% (1e-4) NHEJ event in genomic DNA samples.

In addition to the uncut parental DNA (292 bp), the presence of the cleaved large fragment (~168 bp) and small fragment (~124 bp) indicates cleavage by the Surveyor™ nuclease due to NHEJ-induced modification of DNA sequences and the subsequent formation of DNA heteroduplex during the assay process.

Figure 4A:
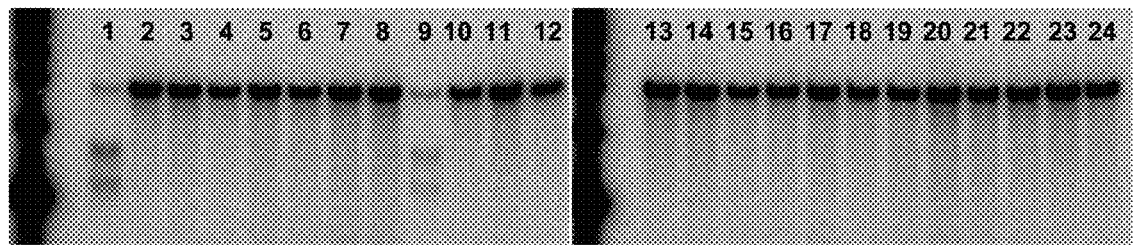
FIG. 4A depicts repair of double-stranded, but not single-stranded, breaks by NHEJ in K562 cells comprising the ZFN pairs indicated above each lane. The lane number corresponds to sample number in Table 1.

Results, as shown in Table 1 and FIG. 4A, demonstrate that the combination of wild-type (WT) ZFNs, 8196zKK+8267EL or 8267RD+8196zDR (lanes labeled 1 and 9), induced DSB, of which 54.3% and 36.7% were repaired by NHEJ, respectively. See, also, FIG. 5B showing NHEJ only with wild-type ZFNs.

By contrast, none of the other ZFN combinations, in which one of the two ZFNs contains catalytically inactivated point mutations in the FokI domain, induced double-stranded breaks, based on the absence of repair by NHEJ as detected by a radioactive Surveyor™ nuclease assay and a highly sensitive Taqman™ qPCR assay. See, FIG. 5B.

TABLE 1

| Sample# | Left ZFN | | Right ZFN | | Estimated TI % | Estimated NHEJ % Nuclease assay | Taqman qPCR |
|---|---|---|---|---|---|---|---|
| 1 | 8267EL | wt | 8196z-KK | wt | 29.4 | 54.3 | 55.3 |
| 2 | 8267EL | wt | 8196z-KK | D467A | 1.1 | 0.0 | 0.0 |
| 3 | 8267EL | wt | 8196z-KK | K469A | 0.0 | 0.0 | 0.0 |
| 4 | 8267EL | D467A | 8196z-KK | wt | 1.6 | 0.0 | 0.0 |
| 5 | 8267EL | K469A | 8196z-KK | wt | 0.7 | 0.0 | 0.0 |
| 6 | 8267EL | D467A | 8196z-KK | D467A | 0.0 | 0.0 | 0.0 |
| 7 | 8267EL | K469A | 8196z-KK | K469A | 0.0 | 0.0 | 0.0 |
| 8 | 8267EL | D467A | 8196z-KK | K469A | 0.0 | 0.0 | 0.0 |
| 9 | 8267RD | wt | 8196z-DR | wt | 28.4 | 36.7 | 34.6 |
| 10 | 8267RD | wt | 8196z-DR | D467A | 0.7 | 0.0 | 0.0 |
| 11 | 8267RD | wt | 8196z-DR | K469A | 0.0 | 0.0 | 0.0 |
| 12 | 8267RD | D467A | 8196z-DR | wt | 2.0 | 0.0 | 0.0 |
| 13 | 8267RD | K469A | 8196z-DR | wt | 0.5 | 0.0 | 0.0 |
| 14 | 8267RD | D467A | 8196z-DR | D467A | 0.0 | 0.0 | 0.0 |
| 15 | 8267RD | K469A | 8196z-DR | K469A | 0.0 | 0.0 | 0.0 |
| 16 | 8267RD | K469A | 8196z-DR | D467A | 0.0 | 0.0 | 0.0 |
| 17 | 8267EL | wt | 8196z-KK | D467A-K469 | 0.6 | 0.0 | 0.0 |
| 18 | 8267EL | wt | 8196z-KK | D450A | 1.9 | 0.0 | 0.0 |
| 19 | 8267EL | D450A | 8196z-KK | wt | 2.5 | 0.0 | 0.0 |
| 20 | 8267EL | D467A-K469 | 8196z-KK | wt | 0.0 | 0.0 | 0.0 |
| 21 | 8267RD | wt | 8196z-DR | D450A | 1.1 | 0.0 | 0.0 |
| 22 | 8267RD | wt | 8196z-DR | D450N | 1.2 | 0.0 | 0.0 |
| 23 | 8267RD | D450N | 8196z-DR | wt | 1.5 | 0.0 | 0.0 |
| 24 | 8267RD | D467A-K469 | 8196z-DR | wt | 0.9 | 0.0 | 0.0 |

Thus, DNA SSBs/nicks induced by ZFN pairs in which one ZFN is catalytically inactivated as described herein are unable to induce NHEJ.

B. Targeted Integration

Targeted integration of various donors was also evaluated. Donors tested included a smaller 46 pb CCR5-patch donor (R5-patch donor), which has a BglI restriction enzyme site and total 46 bp insertion between the 2 CCR5ZFN binding sites; a 1.6 kb CCR5-GFP donor, in which an eGFP expression cassette is flanked by sequence homologous to CCR5 (R5-GFP donor); and an additional donor that replaced the eGFP marker between the homologous CCR5 sequence of the CCR5-GFP donor with a truncated NGFR reporter gene and placed the eGFP marker cassette outside the homologous CCR5 sequence on the donor template plasmid (CCR5-NGFR-outGFP donor). Unless specifically indicated below, the following ZFNs were used: 8267-EL (or ZFN-L-EL), 8267-EL-D450N (or ZFN-L-EL-D450N), 8267-EL-D467A (ZFN-L-EL-D467A), and 8196zKK (ZFN-R-KK).

In the presence of the smaller 46 bp CCR5-patch donor, targeted integration was evaluated by a restriction fragment length polymorphism (RFLP) assay, in which the BglI digested wild-type PCR product is 2433 bp, and the BglI digested fragments of patch-containing modified CCR5 PCR products are 1554bp and 925bp, respectively.

Figure 4B:
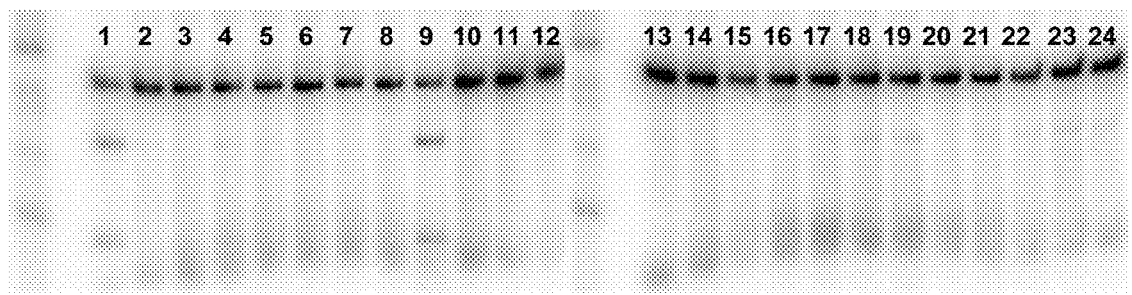
FIG. 4B depicts targeted integration of a 46 bp CCR-5 patch donor molecule following single- or double-stranded cleavage of the CCR-5 gene with the ZFN pairs indicated in Table 1. Lane line numbers correspond to sample numbers.
Figure 4C:
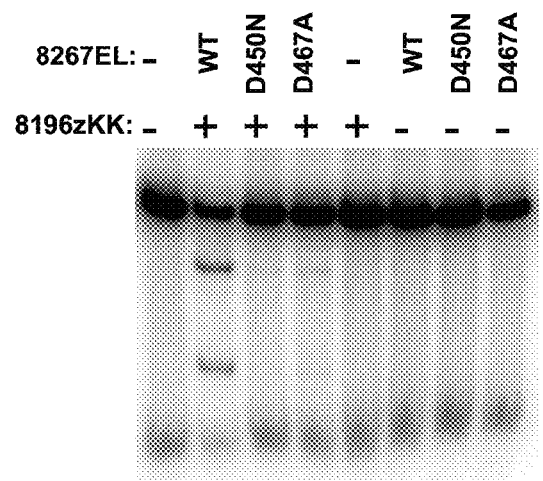
FIGS. 4C and 4D depict homologous recombination events in cells treated with a single zinc finger nuclease or combinations of two zinc finger nucleases (indicated above each lane).
Figure 4D:
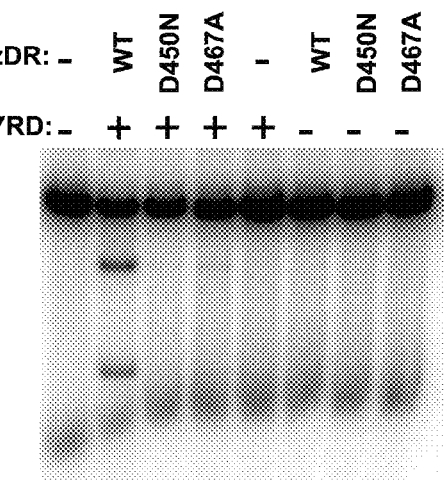

As shown in FIG. 4B and Table 1, the combination of wild-type (WT) ZFNs, 8196zKK+8267EL or 8267RD+ 8196zDR induced DSB, of which 29.4% and 28.4% were repaired by homologous recombination, respectively. The majority of the combinations that contained one wild-type ZFN with a catalytically active FokI domain induced homologous recombination in 0.5-2.5% of the DNA repair events, whereas none of the combinations that contain 2 ZFNs with catalytically inactivated FokI domains were able to induce homologous recombination. Furthermore, all single ZFNs, either having wild-type catalytic activity or catalytically inactivated mutants, failed to induce homologous recombination by themselves (FIGS. 4C and 4D).

Figure 5A:
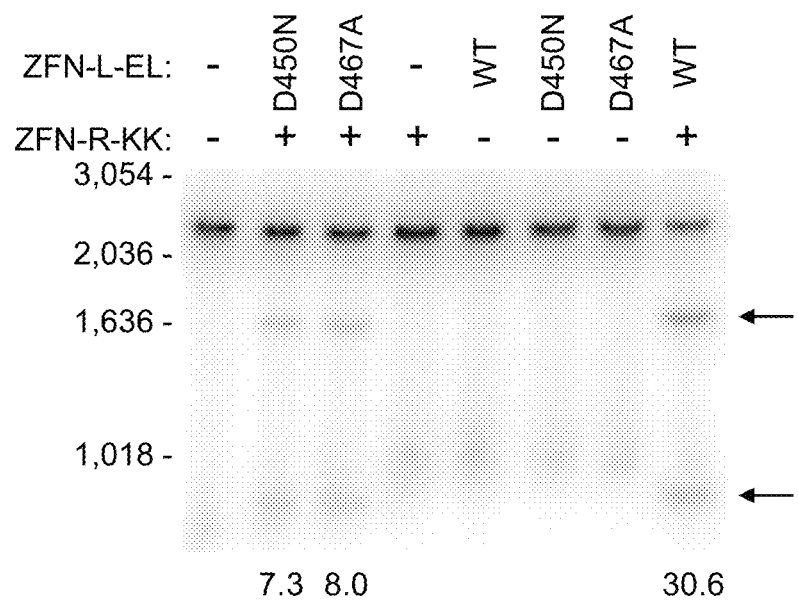
FIG. 5A shows targeted integration analysis and FIG. 5B shows NHEJ analysis. Numbers at the bottom of each lane indicate frequency (%) of targeted integration or NHEJ.
Figure 5B:
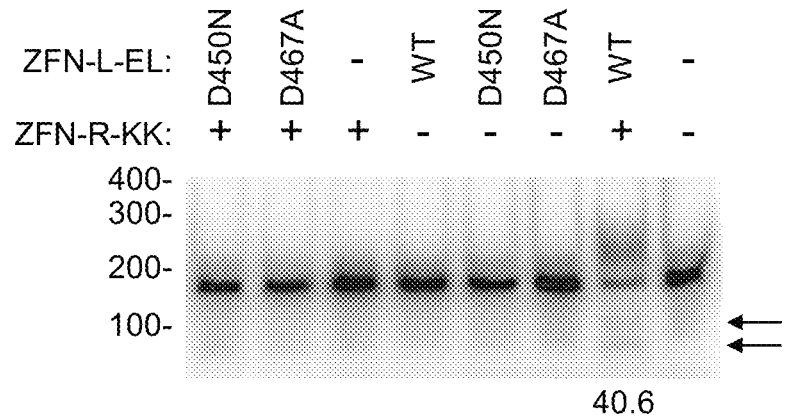

In addition, as shown in FIG. 5A in a separate experiment, K562 cells treated with the WT/WT ZFNs (DSB-inducing) showed targeted integration (TI) of the CCR5-patch donor in 30.6% of the endogenous CCR5 alleles. The cells treated with the D450N/WT or D467A/WT ZFNs also showed TI at the CCR5 locus (7.3 and 8.0%, respectively), but at a ~4-fold reduced level of efficiency. TI could not be detected in any of the samples treated with a single ZFN (WT, D450N, or D467A).

Genotyping of single cell clones derived from unsorted pools in the experiment using the CCR5-patch donor was also performed. K562 cells were co-transfected with the donor DNA indicated in Table 2 and combinations of ZFN expression plasmids: ZFN-L-EL+ZFN-R-KK (WT), ZFN-L-EL-D450N+ZFN-R-KK (D450N), or ZFN-L-EL-D467A+ZFN-R-KK (D467A). Unsorted or sorted pools were subjected to single cell cloning by limited dilution. Single cell-derived clones were selected under microscope and tested by subsequent genotyping analysis.

As shown in Table 2, more than 25% of the expanded clones were heterozygous for targeted integration into the CCR5 locus, confirming the high frequency of HDR-driven genome modification via induction of SSB/nicks in K562 cells.

Similarly, the larger 1.6 kb CCR5-GFP donor described above was introduced into K562 cells along with the WT/WT CCR5 ZFN and nickase mutant ZFN pairs to evaluate targeted integration of the GFP expression cassette into the CCR5 locus. Briefly, GFP+ cells were sorted for by fluorescence activated cell sorting (FACS) at facilities in University of California (Berkeley, Calif.) as described in Moehle et al. (2007) Proc Natl Acad Sci USA 104: 3055-3060, and this sorted population was used to generate single cell-derived clones.

Among the 75 GFP+ clones derived from the sample treated with the WT/WT ZFN (ZFN-L-EL+ZFN-R-KK+ CCR5-GFP), 70 clones (93.3%) harbored TI events and 58 clones (77.3%) harbored NHEJ events. In contrast, the clones modified by treatment with the D450N/WT ZFNs (ZFN-L-EL-D450N+ZFN-R-KK+CCR5-GFP) showed no NHEJ-based modification, whereas 61 (65.6%) of the total 93 clones exhibited a TI event. One out of 95 clones (1.1%) derived from the cells treated with D467A/WT ZFNs (ZFN-L-EL-D467A+ZFN-R-KK+CCR5-GFP) showed an NHEJ-like mutation at CCR5, whereas 67 clones (70.5%) exhibited a TI event. See, Table 2.

For experiments using the CCR5-tNGFR-outGFP donor, cells undergoing HDR-driven TI of the sequence encoded on the donor should only express the NGFR marker, but not GFP(NGFR+GFP−). Expression of eGFP (GFP+) would indicate the presence of episomal DNA or random integration of the donor plasmid at unknown sites.

To enrich cells with surface NGFR expression, cells were first incubated with anti-NGFR mAb (BD Pharmingen), washed, and then incubated with goat anti-mouse IgG conjugated with Dynal beads provided in the CELLection Pan mouse IgG kit (Invitrogen), followed by passing through magnetic fields. Beads were then removed from enriched cells by DNase I digestion following manufacture's instruction (Invitrogen). Alternatively, cells were either unstained or incubated with anti-NGFR mAb conjugated with PE (BD Pharmingen), then sorted based on GFP and/or NGFR expression levels using a flow cytometric cell sorter.

Figure 6A:
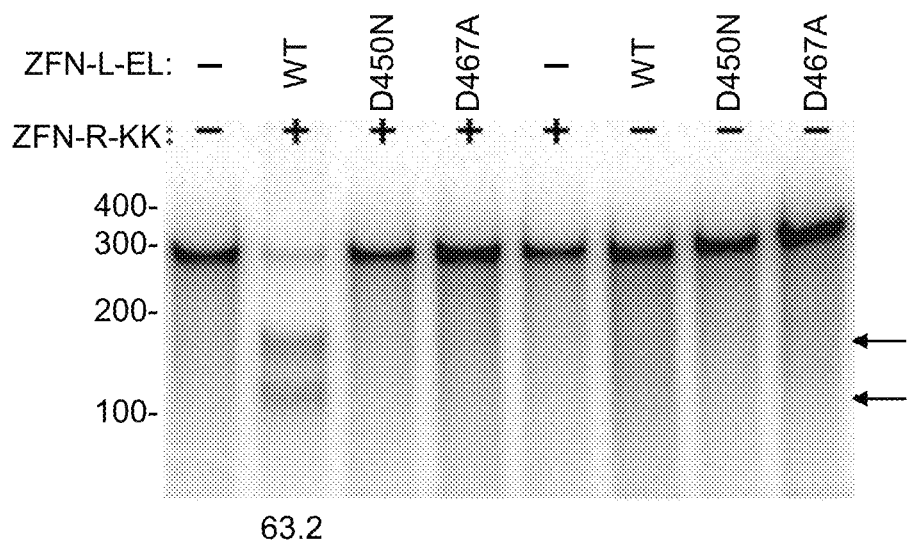
FIG. 6A shows NHEJ analysis and FIG. 6B shows targeted integration analysis by Southern blot. Numbers at the bottom of each lane indicate frequency (%) of targeted integration or NHEJ.

The sorted NGFR+GFP−-cell pool derived from cells treated with WT/WT ZFNs (ZFN-L-EL+ZFN-R-KK+ CCR5-tNGFR-outGFP) contained a high level (63.2%) of NHEJ-based modification, whereas no NHEJ modification was detected in cells treated with the following ZFNs: D450N/WT (ZFN-L-EL-D450N+ZFN-R-KK+CCR5-tNGFR-outGFP) or D467A/WT (ZFN-L-EL-D467A+ZFN-R-KK+CCR5-tNGFR-outGFP), as determined by the Surveyor™ nuclease assay (FIG. 6A). This difference in the level of modification by NHEJ was also observed both in the sorted NGFR+GFP+ cell population and unsorted pools.

Figure 6B:
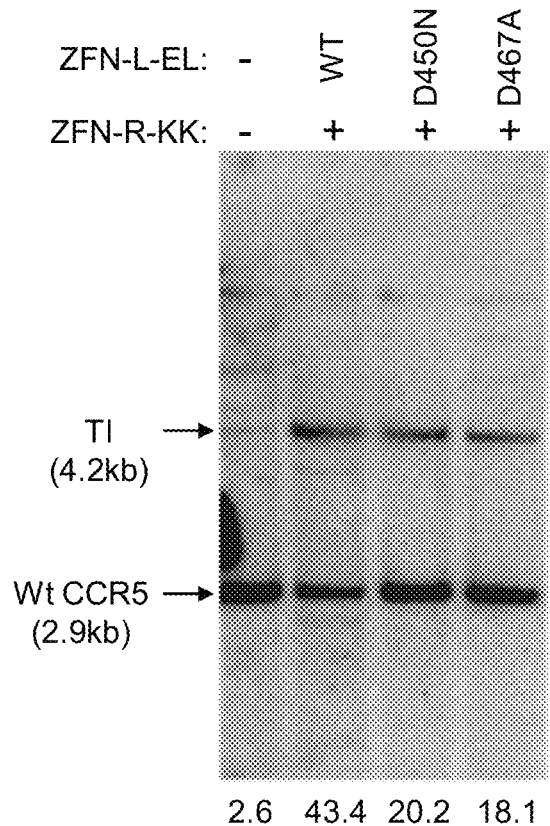

While the cells treated with the CCR5-tNGFR-outGFP donor and nick-inducing ZFNs (D450N/WT or D467A/WT) did not exhibit NHEJ using the Surveyor™ nuclease assay, we found >18% of the CCR5 alleles in the sorted NGFR+ GFP− cells derived from these samples harbored a targeted insertion event, as detected by Southern blot (FIG. 6B). Furthermore, single cell-derived clones generated from samples treated with the D450N/WT and D467A/WT ZFNs confirmed that 71 out of 91 (78%) and 74 out of 96 (77.1%) clones have TI in their genomes, respectively (Table 2). In contrast, no TI events were seen in the sorted NGFR+GFP+ cells, which would enrich for cells that had undergone random integration of the donor plasmid, derived from the ZFN-treated samples. Multiple Southern blot bands were seen in the sorted NGFR+GFP+ cells derived from the WT/WT ZFN (ZFN-L-EL+ZFN-R-KK+CCR5-tNFR-outGFP)-treated sample, in addition to the expected TI band, presumably caused by the presence of various kinds of NHEJ modification at CCR5, random integration of the donor DNA template, or stable persistence of the donor plasmid as episomal DNA.

As shown in Table 2, more than 25% of the expanded clones were heterozygous for targeted integration into the CCR5 locus, confirming the high frequency of HDR-driven genome modification via induction of SSB/nicks.

TABLE 2

| Pools | Donor | ZFN | Total clones | TI clones | TI clones % | NHEJ clones | NHEJ clones % |
|---|---|---|---|---|---|---|---|
| Unsorted | R5-Patch | D450N | 283 | 73 | 25.8% | ND | ND |
| Unsorted | R5-Patch | D467A | 284 | 86 | 30.3% | ND | ND |
| GFP+ | R5-GFP | WT | 75 | 70 | 93.3% | 58 | 77.3% |
| GFP+ | R5-GFP | D450N | 93 | 61 | 65.6% | 0 | 0.0% |

TABLE 2-continued

| Pools | Donor | ZFN | Total clones | TI clones | TI clones % | NHEJ clones | NHEJ clones % |
|---|---|---|---|---|---|---|---|
| GFP+ | R5-GFP | D467A | 95 | 67 | 70.5% | 1 | 1.1% |
| NGFR+GFP− | R5-NGFR-outGFP | WT | 83 | 79 | 95.2% | ND | ND |
| NGFR+GFP− | R5-NGFR-outGFP | D450N | 91 | 71 | 78.0% | ND | ND |
| NGFR+GFP− | R5-NGFR-outGFP | D467A | 96 | 74 | 77.1% | ND | ND |

Thus, single-stranded breaks (nicks) in DNA can induce homologous recombination in mammalian (e.g., human) cells, and can be used for targeted integration of any DNA sequences, with reduction or elimination of on or off-target NHEJ mutations at the ZFN cleavage sites.

Example 5

Solexa® Deep Sequencing

To further evaluate whether SSB/nicks are repaired by the NHEJ pathway, we performed Solexa® deep sequencing of the CCR5 target locus from WT/WT, D450/WT ZFNs, or control treated K562 cells. Briefly, genomic DNAs were amplified use a pair of CCR5 primers located outside the CCR5 homologous region of donor molecules. The amplified 2.5 kb CCR5 fragments were gel purified and used as templates for inside PCR reactions using primers containing BpmI and XhoI restriction enzyme sites.

The amplicons were then digested with BpmI and XhoI to remove the 5'-end of 16bp of the PCR products to allow sequencing to begin close to the putative ZFN cleavage sites. The digested products were gel purified and ligated to adaptors which have BpmI- or XhoI-digested DNA-like ends and containing no tag or a three-nucleotide 'bar-code' unique to each experiment. Adaptor-ligated PCR products were then gel purified and PCR amplified using Illumina Genomic DNA Primers (Illumina). The resulting PCR products were subjected to Solexa® deep sequencing located at California Institute for Quantitative Biosciences, University of California (Berkeley, Calif.). A custom-written computer script was used to extract all sequences which were either WT or consistent with NHEJ mediated deletions or insertions.

Greater than 485,000 quality sequence reads (>99% confidence for each base) were analyzed from each of the samples tested. The sequences derived from the WT/WT ZFN sample (ZFN-L-EL+ZFN-R-KK+CCR5-patch) showed that 260,509 out of 713,186 sequences (36.5%) appeared to be modified by NHEJ. See, Table 3.

TABLE 3

Solexa® deep sequencing of unsorted pools

| ZFN-L | ZFN-R | Total | WT | Ins | Uni-Ins | Del | Uni-Del | Ins + Del | Ins + Del % |
|---|---|---|---|---|---|---|---|---|---|
| none | none | 1772351 | 1772256 | 0 | 0 | 24 | 14 | 24 | 0.0014 |
| EL | KK | 713186 | 427922 | 68594 | 91 | 191915 | 500 | 260509 | 36.5275 |
| EL-D450N | KK | 944605 | 944492 | 18 | 2 | 25 | 13 | 43 | 0.0046 |
| EL | none | 549766 | 549698 | 8 | 2 | 24 | 11 | 32 | 0.0058 |
| EL-D450N | none | 495811 | 495766 | 0 | 0 | 0 | 0 | 0 | 0.0000 |
| none | KK | 485162 | 485103 | 6 | 1 | 10 | 7 | 16 | 0.0033 |

*"WT" refers to wild-type;
"Ins" refers to insertions;
"Del" refers to deletions;
"Uni" refers to unique insertions or deletions In sharp contrast, the sequences analyzed from the D450/WT ZFNs (ZFN-L-EL-D450N+ZFN-R-KK+CCR5-patch) revealed that only 43 out of 944,605 sequences (0.0046%) exhibited mutations consistent with NHEJ, a >7,900 fold reduction in NHEJ. The mutation rate in the D450/WT ZFN treated cells is within the background noise of the assay (0-0.0058%), which is presumably caused by errors generated during the PCR amplification and sequencing steps, based on data from samples treated with donor DNA only or donor and a single ZFN. This is also supported by the small number of unique sequence variants identified in the control and ZFN samples. A greater diversity in the types of sequence modifications observed would be expected, as seen in the WT/WT ZFN-treated sample, if these modifications were due to NHEJ.

The cells treated with D450N/WT ZFNs in the presence of CCR5-patch donor harbored 7.3% targeted integration events, meaning there is a >1,500 fold preference for HDR over NHEJ using the ZFNs. It should be noted that the addition of a single ZFN does not cause modification of the locus by NHEJ, providing additional evidence that the binding of 2 ZFNs in the appropriate orientation on DNA is required for DSB formation.

These data suggested that there are either no or extremely low levels of NHEJ events in SSB-inducing ZFN-treated samples. These data further confirm that SSB/nicks are selectively repaired by HDR and not NHEJ.

Example 6

Genome-wide Assessment of DSB Formation Induced by ZFN Pairs with a Catalytically Inactivated ZFN SSB/nicks are one of the most frequent types of DNA damage produced by endogenous reactive oxygen species or during DNA metabolism, such as DNA repair and replication, which can be repaired precisely by DNA polymerases and ligases using the intact opposite strand as a template. See, Caldecott (2008) *Nat Rev Genet.* 9:619-31. To further evaluate the potential for SSB-generating ZFNs to induce a low level of DSBs at genomic sites other than the intended target site, we performed a genome-wide assessment of DSB formation by detecting $\gamma H_2AX$ and 53BP1 expression, since $\gamma H_2AX$ and 53BP1 are recruited to the site of DSBs as the natural response to DNA damage.

Briefly, for intracellular staining of γH2AX, cells collected at various time points (e.g., 1, 2, 3 and 7 days) post-nucleofection were permeabilized with perm/wash buffer (0.05% Saponin, 2.5% FBS, and 0.02% NaN3 in PBS) and then incubated with anti-γH2AX monoclonal antibody (Upstate) followed by incubation with Alexa Fluor488-conjugated goat anti-mouse immunoglobulin (Ig, Invitrogen). Cells were then analyzed using a Guava Easycyte® single cell analysis system (Guava® Technologies).

For 53BP1 immunocytochemistry, cells were collected to prepare slides by cytospin (Thermo Scientific) and stained with anti-53BP1 rabbit polyclonal antibodies (Bethyl Laboratories) followed by taking pictures with a CCD camera connected to an immunofluorescence microscope (Nikon) as described before in detail in Perez et al. (2008) *Nat Biotechnol* 26:808-16.

Figure 7:
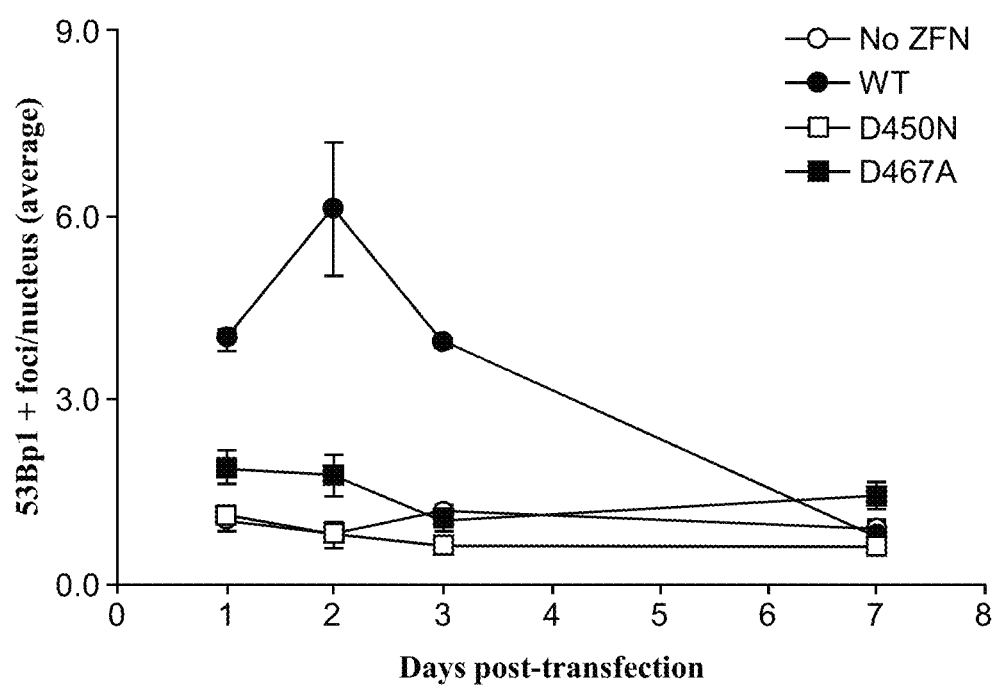
FIG. 7 is a graph depicting 53BP1+foci (indicative of DSBs) at the indicated time points in K562 cells transfected with the indicated ZFN constructs. Open circles depict control cells having no ZFNs; shaded circles show cells transfected with wild-type ZFNs; open squares show cells transfected with one wild-type ZFN and one inactivated ZFN (D450N); and shaded squares show cells transfected with one wild-type ZFN and one inactivated ZFN (D467A).

Under the experimental conditions used to transfect cells with ZFNs and donor, a significant amount of $\gamma H_2AX$ expression was observed in cells treated with WT/WT ZFNs (ZFN-L-EL+ZFN-R-KK+CCR5-patch, 14.70% $\gamma H_2AX^+$) at 2 days post-transfection, but not in cells treated with D450N/WT (ZFN-L-EL-D450N+ZFN-R-KK+CCR5-patch, 0.33% $\gamma H_2AX^+$). However, slightly higher $\gamma H_2AX$ expression was observed in cells treated with D467A/WT (ZFN-L-EL-D467A+ZFN-R-KK+CCR5-patch, 4.34% $\gamma H_2AX^+$), consistent with the previous observation that the D467A/WT pair may retain a small amount of DSB activity. As expected, more 53BP1$^+$ foci were also observed in cells treated with WT/WT ZFNs (ZFN-L-EL+ZFN-R-KK+CCR5-patch, 6.09±1.07 foci/cell, Ave±SD) than in cells treated with the D450N/WT pair (ZFN-L-EL-D450N+ZFN-R-KK+CCR5-patch, 0.84±0.17 foci/cell), which is essentially at the level of background. A moderate increase in the number of 53BP1$^+$ foci was observed in cells treated with D467A/WT (ZFN-L-EL-D467A+ZFN-R-KK+CCR5-patch, 1.77±0.33 foci/cell), compared to the control cells transfected with the CCR5-patch donor alone (0.82±0.22 foci/cell). The expression of $\gamma H_2AX$ and 53BP1 returned to background levels within a week after transfection (FIG. 7).

The absence of upregulated $\gamma H_2AX$ and 53BP1 expression under these experimental conditions further confirm that ZFNs as described herein do not increase the number of DSBs formed over background and provides additional support that the targeted integration observed in the SSB-inducing ZFN-treated cells does occur through nick-induced HDR, not DSB-induced HDR, and providing an alternative method for editing the genome of human cells while reducing the potential for both on-target and off-target mutagenesis via NHEJ.

Example 7

SSB-ZFN-initiated Targeted Integration in a Non-CCR5 Endogenous Locus

To further evaluate whether ZFNs that induce a SSB can be used for genome editing at loci other than the CCR5 locus, we tested D450N ZFNs-initiated targeted integration at the CXCR4 locus. WT and D450N ZFNs including zinc finger domains targeted to CXCR4 were prepared as described in U.S. Application No. 61/210,636. Subsequently, K562 cells were nucleofected with a CXCR4-patch donor DNA in the absence (No ZFN) or presence of CXCR4D450N ZFNs: CXCR4-ZFN-L-EL-D450N+CXCR4-ZFN-R-KK. Cells were allowed to recover for 4-7 days and then nucleofected again with the same DNAs. The process was repeated for a total of 4 nucleofections. Cells were then collected 3 days after the last nucleofection for gDNA preparation and RFLP assay.

Figure 8:
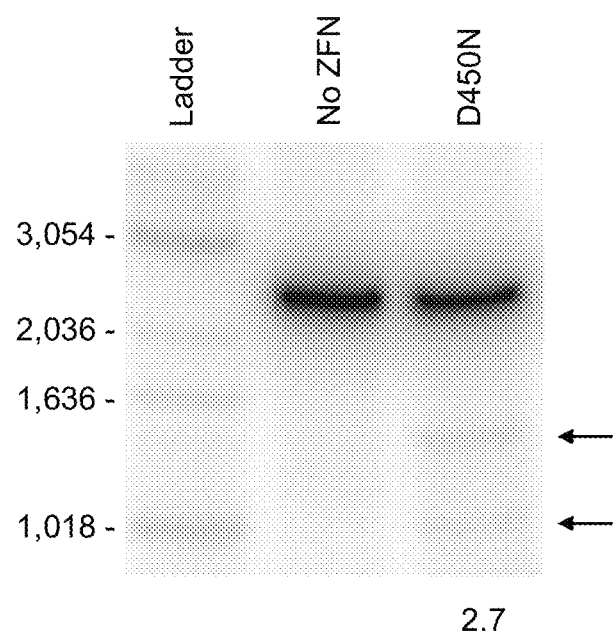
FIG. 8 depicts analysis of targeted integration at the CXCR4 locus in K562 cells. K562 cells were nucleofected with a CXCR4-patch donor DNA in the absence (no ZFN) or presence of CXCR4 D450N ZFNs: CXCR4-ZFN-L-EL-D450N+CXCR4-ZFN-R-KK. Cells were allowed to recover for 4-7 days and then nucleofected again with the same DNAs. The process was repeated for a total of 4 nucleofections. Cells were then collected 3 days after the last nucleofection for gDNA preparation and RFLP assay. Expected positions of CXCR4 modified by TI were indicated by arrows. Numbers at the bottom of each lane indicate frequency (%) of TI.

As shown in FIG. 8, D450N/WT ZFN pairs specifically targeting the endogenous CXCR4 gene located on chromosome 2 in the human genome can also mediate a significant amount of TI at the CXCR4 locus.

These data suggests that the strategy of using targeted SSB-inducing ZFNs to mediate HDR-driven genome editing may be broadly applicable and could be universally applied across different target loci.

Example 8

Detection of Nucleic Acid Sequences

Blood or cell samples suspected of containing an infectious agent or from an individual suspected of having a genetic disease are collected according to standard techniques. Appropriate primers are prepared for a target nucleotide sequence that is characteristic of the genetic disease or infectious agent. Nucleases as described herein are constructed to induce a site-specific single-stranded nick in the target sequence and/or amplification primer.

The samples are incubated with the appropriate primers, nucleotides (dNTPs for amplification) and enzyme mix (containing the appropriate nicking nucleases and a DNA polymerase) such that, when present, the sequence characteristic of the genetic disease or infectious agent is amplified. One or more components may detectably labeled for ease of detection.

The amplified sequence, if any, is then detected using standard techniques, for example, gel electrophoresis, flow cytometry, radiolabeling, etc. The presence of an amplified sequence is indicative of the presence of the genetic disease or infectious agent.

Example 9

Detection of Nucleic Acid Sequences

Blood or cell samples suspected of containing an infectious agent or from an individual suspected of having a genetic disease are collected according to standard techniques.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An artificial nuclease comprising
   (i) first and second cleavage domains from an endonuclease, wherein the first cleavage domain is catalytically inactive and the second cleavage domain is catalytically active; and
   (ii) a DNA-binding molecule that is heterologous to the first and second cleavage domains, and further wherein the DNA-binding molecule of the nuclease binds to a target sequence in a double-stranded genome and the nuclease induces a site-specific single-stranded break at or near the target sequence in the double-stranded genome such that the double-stranded genome is modified.

2. The nuclease of claim 1, wherein the modification is selected from the group consisting of insertions, deletions and combinations thereof.

3. The nuclease of claim 2, wherein modification results in inactivation of an endogenous gene.

4. The nuclease of claim 2, wherein the modification comprises targeted integration of an exogenous sequence.

5. A composition comprising the nuclease of claim 1.

6. An isolated cell or cell line comprising a nuclease of claim 1.

7. A method of generating a single-stranded break in a target double-stranded sequence in cellular chromatin of a cell, the method comprising:
   providing a nuclease according to claim 1 to the cell such that the nuclease generates a single-stranded break in the target double-stranded sequence in cellular chromatin.

8. The method of claim 7, further comprising providing an exogenous sequence to the cell such that the exogenous sequence is inserted into the cellular chromatin at or near the single-stranded break.

9. The method of claim 8, wherein the exogenous sequence replaces a wild-type genomic sequence.

10. The method of claim 7, wherein a target sequence in the cellular chromatin is inactivated.

11. The method of claim 7, further comprising providing a second nuclease that makes a second single-stranded break in the double-stranded cellular chromatin.

12. A cell made by the method of claim 7.

* * * * *